(12) United States Patent
Jhung et al.

(10) Patent No.: US 6,180,822 B1
(45) Date of Patent: Jan. 30, 2001

(54) METHOD OF PRODUCING AROMATIC CARBOXYLIC ACIDS BY OXIDIZING ALKYL AROMATIC COMPOUNDS OR PARTIALLY OXIDIZED INTERMEDIATES THEREOF WITH CARBON DIOXIDE CONTAINING GAS

(75) Inventors: Sung-Hwa Jhung; Ki-Hwa Lee; Youn-Seok Park, all of Taejeon (KR); Jin Sun Yoo, Flossmoor, IL (US)

(73) Assignee: Samsung General Chemical Co., Ltd., Seosan (KR)

( * ) Notice: Under 35 U.S.C. 154(b), the term of this patent shall be extended for 0 days.

(21) Appl. No.: 09/453,536

(22) Filed: Dec. 3, 1999

(30) Foreign Application Priority Data

Dec. 22, 1998 (KR) .................................................. 98/57388
Apr. 28, 1999 (KR) .................................................. 99/15250

(51) Int. Cl.⁷ .................................................. C07C 51/16
(52) U.S. Cl. .......................................... 562/412; 562/413
(58) Field of Search ...................................... 562/412, 413

(56) References Cited

U.S. PATENT DOCUMENTS

| | | | |
|---|---|---|---|
| 2,833,816 | 5/1958 | Saffer et al. | 260/524 |
| 3,584,039 | 6/1971 | Meyer | 260/525 |
| 5,112,992 | 5/1992 | Belmonte et al. | 549/245 |
| 5,183,933 | 2/1993 | Harper et al. | 562/414 |
| 5,324,702 | 6/1994 | Yoo et al. . | |
| 5,359,133 | 10/1994 | Nazimok et al. . | |
| 5,371,283 | 12/1994 | Kingsley et al. . | |
| 5,453,538 | 9/1995 | Broeker et al. . | |
| 5,523,474 | 6/1996 | Kingsley et al. . | |
| 5,596,129 | 1/1997 | Murashige et al. . | |
| 5,693,856 | 12/1997 | Ramachandran et al. | 562/414 |
| 5,696,285 | 12/1997 | Roby . | |

FOREIGN PATENT DOCUMENTS

WO 96/41791    12/1996  (WO) .

OTHER PUBLICATIONS

J. Yoo, "Selective Gas–Phase Oxidation at Oxide Nanoparticles on Microporous Materials," Catalysis Today, vol. 41 (1998), pp. 409–432.

J. Yoo, "Gas Phase Oxygen Oxidation of Alkylaromatics over CVD Fe/Mo/Borosilicate Molecular Sieve, Fe/Mo/DBH. VII. Oxidative Dehydrogenation of Alkylaromatics," Applied Catalysis A: General, vol. 142 (1996), pp. 19–29.

J. Yoo, "The CVD Fe/Mo/DBH (Deboronated Borosilicate Molecular Sieve)—Catalyzed Oxidation Reactions," Applied Catalysis A: General, vol. 143 (1996), pp. 29–51.

J. Yoo, "Gas–Phase Oxygen Oxidations of Alkylaromatics over CVD Fe/Mo/Borosilicate Molecular Sieve. VI. Effects of para–Substituents in Toluene Derivatives," Applied Catalysis A: General, vol. 135 (1996), pp. 261–271.

J. Yoo, et al., "Gas–Phase Oxygen Oxidations of Alkylaromatics over CVD Fe/Mo/Borosilicate Molecular Sieve. II. The Role of Carbon Dioxide as a Co–Oxidant," Applied Catalysis A: General, vol. 106 (1993), pp. 259–273.

G. Zajac, et al., "Characterization and Oxidation Catalysis of Alkylaromatics over CVD Fe/Mo/Borosilicate Molecular Sieve: Fe/Mo/DBH," Journal of Catalysis, vol. 151, No. 2, Feb. 1995, pp. 338–348.

W. Partenheimer, "Methodology and Scope of Metal/bromide Autoxidation of Hydrocarbons," J. Chem Soc. Chem. Commun., vol. 23 (1995), pp. 69–158.

M. Aresta, et al., "Carbon Dioxide as Modulator of the Oxidative Properties of Dioxygen in the Presence of Transition Metal Systems," J. Chem. Soc. Chem. Commun., 1992, pp. 315–317.

*Primary Examiner*—Paul J. Killos
(74) *Attorney, Agent, or Firm*—Fitzpatrick, Cella, Harper & Scinto

(57) ABSTRACT

An improved production method of aromatic carboxylic acid products of significantly improved yield and quality, the method including oxidizing alkyl aromatic substrates or their partially oxidized intermediates in a catalyst system containing a conventional catalyst and, if deemed necessary, additional components such as a transition metal or lanthanide series metal, in an acetic acid medium, with a feed gas containing both oxygen and carbon dioxide. Since carbon dioxide functions as a co-oxidant along with oxygen in the oxidation reaction, the oxidation reaction proceeds more selectively to produce the carboxylic acid product much faster under milder reaction conditions as compared to the conventional oxidation. The present invention also can be utilized as an effective purification process to produce highly pure terephthalic acid or isophthalic acid by oxidation of impurities such as 4-carboxybenzaldehyde and para-toluic acid or 3-carboxybenzaldehyde and meta-toluic acid which are contaminated in crude terephthalic acid and isophthalic acid products, respectively.

22 Claims, No Drawings

METHOD OF PRODUCING AROMATIC CARBOXYLIC ACIDS BY OXIDIZING ALKYL AROMATIC COMPOUNDS OR PARTIALLY OXIDIZED INTERMEDIATES THEREOF WITH CARBON DIOXIDE CONTAINING GAS

INCORPORATION BY REFERENCE

This application incorporates by reference a U.S. patent application being filed concurrently herewith on Dec. 3, 1999, entitled "A METHOD OF PRODUCING AROMATIC CARBOXYLIC ACIDS BY OXIDIZING ALKYL AROMATIC HYDROCARBONS OR PARTIALLY OXIDIZED INTERMEDIATES THEREOF" by Applicants Sung-Hwa Jhung, Youn-Seok Park, Ki-Hwa Lee, Jin-Sun Yoo, and Jong-Hyun Chae, application Ser. No. 09/453,537.

BACKGROUND OF THE INVENTION

1. Field of the Invention

The present invention discloses an improved process for oxidizing alkyl aromatic hydrocarbons and/or their partially oxidized intermediates to produce aromatic carboxylic acids. The process involves the liquid phase oxidation in the presence of a catalyst of cobalt-manganese-bromine in an aliphatic carboxylic acid having 1–6 carbon atoms such as acetic acid as a solvent with a gas containing oxygen and carbon dioxide. Furthermore, an additional transition metal or lanthanide series metal is introduced to the cobalt-manganese-bromine catalyst system, when deemed necessary.

The rate of the oxidation reaction of an alkyl aromatic substrate was remarkably increased in the present process over the conventional oxidation process. The yield and quality of the carboxylic acid products were also significantly improved in the process. Thus, for example, terephthalic acid and isophthalic acid of improved yield and purity are produced by carrying out the oxidation of para-xylene and meta-xylene, respectively, in the co-presence of carbon dioxide and oxygen under relatively mild reaction conditions.

2. Description of the Related Art

As discussed below, methods of manufacturing aromatic carboxylic acids are well known and widely used commercially. For example, the method of manufacturing of aromatic carboxylic acids such as terephthalic acid (TPA), isophthalic acid (IPA), phthalic acid, phthalic anhydride, naphthalene dicarboxylic acid, trimellitic acid, trimellitic anhydride, trimesic acid, pyromellitic dianhydride, 4,4'-biphenyldicarboxylic acid and benzoic acid by oxidizing alkylaromatic compounds or the oxidized intermediates thereof, in the presence of cobalt-manganese-bromine, from such alkylaromatic compounds as para-xylene, para-tolualdehyde, para-toluic acid, 4-carboxybenzaldehyde (4-CBA), meta-xylene, meta-tolualdehyde, meta-toluic acid, 3-carboxybenzaldehyde, ortho-xylene, dimethylnaphtalene, pseudocumene (1,2,4-trimethylbenzene), mesitylene (1,3,5-trimethylbenzene), durene (1,2,4,5-tetramethylbenzene), 4,4'-dimethylbiphenyl and toluene is well known (for example, U.S. Pat. Nos. 2,833,816 and 5,183,933). Such aromatic carboxylic acids are used as raw materials for manufacturing polyester after appropriate purification such as hydrogenation, etc. (U.S. Pat. No. 3,584,039). Also, polyester is widely used as a synthetic fiber, film, etc.

There were continuous endeavors to develop a catalyst system with high efficiency and enhanced reactivity to manufacture aromatic carboxylic acids. The newly developed technologies, however, were not practical due to the increase in side reactions, price of catalyst, difficulty of operation, precipitation of catalyst, etc.

Improvements in the efficiency of the reaction for manufacturing of aromatic carboxylic acids are very significant because they may improve productivity, quality and cost competitiveness due to the reduction in the reaction time and side reactions. In other words, it is highly desirable to develop a technology to increase the efficiency of the oxidation reaction of alkyl aromatic compounds and the oxidized intermediates thereof by means of an improvement in the reaction processes.

There were many attempts to increase the efficiency by adding a third metal catalyst to the cobalt-manganese-bromine catalyst system which is the basic catalyst system, to enhance the catalyst efficiency during the manufacturing of aromatic carboxylic acids. The added metals were mainly transition metals, and by adding, for example, hafnium, zirconium, molybdenum, etc., the reactivity therein was increased (U.S. Pat. No. 5,112,992).

On the other hand, an oxygen containing gas such as air was mainly used as an oxidant during the manufacturing of aromatic carboxylic acids. Carbon dioxide was not used as an oxidant due to its chemical stability. Yet, in the research for improving the process efficiency, there was a case in which chemically stable carbon dioxide, recycled from the reaction vent gas, was injected to the reactor to increase the stability in the process by mitigating the problematic possibilities of explosion due to oxygen when using pure oxygen or gas containing pure oxygen or oxygen enriched gas as an oxidant (U.S. Pat. No. 5,693,856). Nevertheless, the case is not known in which carbon dioxide was added to improve the reaction efficiency and the effects of the concentration of added carbon dioxide on oxidation.

In summary, the basic oxidation technology for manufacturing carboxylic acids, especially for TPA manufacture, has been extensively developed. The basic process technology is now approaching a point of diminishing returns, and further major breakthroughs i.e., new catalyst systems, raw materials, and basic unit operations, are not anticipated. The leading producers are expected to have greater optimization and energy integration across the entire production complex with more advanced control schemes. However, surpassing the current general expectation, the present invention have made a remarkable breakthrough to achieve the improved catalyst activity and selectivity toward aromatic carboxylic acids, especially for terephthalic acid and isophthalic acid, in the aforementioned catalyst composition under milder oxidation conditions.

SUMMARY OF THE INVENTION

As a result of research for resolving the above problems, the inventors herein added an appropriate amount of carbon dioxide to the oxygen containing gas, which was supplied as an oxidant in the oxidation reaction, in the manufacturing of aromatic carboxylic acids in the catalyst of cobalt-manganese-bromine, in which a transition metal or lanthanide metal was added as deemed necessary. The reactivity not only dramatically increased but the side reactions also decreased. Based on such findings, the present invention has been thus perfected.

In view of the foregoing, in one aspect, the present invention relates to a method of producing an aromatic carboxylic acid, the method comprising the steps of oxidizing an alkyl aromatic compound or a partially oxidized intermediate thereof, with a gas (e.g., a feed gas or a reaction gas) comprising oxygen and carbon dioxide, using a catalyst comprising cobalt, manganese, and bromine. Preferably, the carbon dioxide is present in the gas in an amount of at least 4% by volume of the gas.

In another aspect, the present invention relates to a method of producing an aromatic carboxylic acid, the method comprising the steps of oxidizing an alkyl aromatic compound or a partially oxidized intermediate thereof, with a gas comprising oxygen and an effective amount of carbon dioxide, the effective amount being an amount sufficient to exhibit action by the carbon dioxide as a co-oxidant (e.g., an amount greater than that present in air, or as in the examples hereinbelow), using a catalyst comprising at least one transition metal. Preferably, the carbon dioxide is present in the gas phase in an amount of at least 1% by volume of the gas phase, or at least 4% by volume, or at least 7% by volume, or at least 14% by volume, or at least 50% by volume.

In another aspect, the present invention relates to a method of liquid phase $O_2$ oxidation of alkylaromatics such as p-, m-, and o-xylenes to the corresponding terephthalic acid, isophthalic acid, and phthalic anhydride with the MC-type catalyst, Co—Mn—Br, in the co-presence of $CO_2$, e.g.,

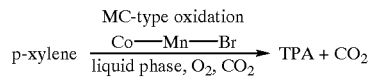

In a still further aspect, the present invention relates to a process of purifying crude terephthalic acid products or crude isophthalic acid products containing, as an impurity, a partially oxidized intermediate of an alkyl aromatic compound, to obtain substantially pure terephthalic acid or isophthalic acid by using an above-discussed method.

In still further aspects, the present invention relates to (a) an aromatic carboxylic acid prepared by an above-discussed method, (b) polyester made using the aromatic carboxylic acid, and (c) a product made using the polyester.

These and other aspects, objects, advantages, and features of the present invention will become apparent from the following detailed description of preferred embodiments thereof.

Unless otherwise stated, in this application, the concentration of gas is in volume %, the concentration of the catalyst is in weight ppm (by total weight of the reaction mixture), and the concentration of the product, and any other unspecified %, is in weight %.

DESCRIPTION OF THE PREFERRED EMBODIMENTS

The present invention relates to a production method of aromatic carboxylic acids, wherein alkylaromatic compounds or the oxidized intermediates thereof are oxidized by an oxygen containing gas, with an aliphatic carboxylic acid having 1–6 carbon atoms as a solvent, in the presence of a catalyst of cobalt-manganese-bromine, with addition of a transition metal or lanthanide metal as deemed necessary. In the process, an appropriate amount of carbon dioxide is added to the oxygen containing gas, which is supplied as an oxidant.

Starting substances, i.e., alkylaromatic compounds or the oxidized intermediates thereof, to be oxidized in the present invention are preferably the compounds of benzene, naphthalene or similar aromatic compounds having one or more than one substituted alkyl groups (or a functional group having an oxidized alkyl group), such as para-xylene, para-tolualdehyde, para-toluic acid, 4-carboxybenzaldehyde, meta-xylene, meta-tolualdehyde, meta-toluic acid, 3-carboxybenzaldehyde, ortho-xylene, dimethylnaphthalene, pseudocumene (1,2,4-trimethylbenzene), mesitylene (1,3,5-trimethylbenzene), durene (1,2,4,5-tetramethylbenzene), pentamethylbenzene, hexamethylbenzene, 4,4'-dimethylbiphenyl, and toluene.

The intended substances of the present invention i.e., aromatic carboxylic acids, are preferably the compounds of benzene, naphthalene or similar aromatic compounds having one or more than one substituted carboxylic acid groups (or anhydrides with the removal of water by condensation of the carboxylic groups), such as terephthalic acid, isophthalic acid, phthalic acid, phthalic anhydrides, naphthalene dicarboxylic acid, trimellitic acid, trimellitic anhydrides, trimesic acid, pyromellitic dianhydride, 4,4'-biphenyldicarboxylic acid, and benzoic acid.

As for the basic catalyst in the present invention, a cobalt-manganese-bromine catalyst system was used. If deemed necessary, a transition metal or lanthanide metal component may be added. In the basic catalyst, the atomic weight ratio of manganese/cobalt is preferably 0.1~10, or more preferably 0.5~5. The atomic weight ratio of bromine/(manganese+cobalt) is preferably 0.1~10, or more preferably 0.5~2. The concentration of cobalt is preferably 20~10,000 ppm of the weight of the reactants (i.e., the substrate (the starting substance to be oxidized such as the alkylaromatic compound), the solvent, and the catalyst), or more preferably 50~10,000 ppm.

As for the source of bromine, it could be a bromine compound, such as hydrogen bromide, tetrabromoethane, etc. As for the source of manganese and cobalt, a compound which is soluble in solvents, such as acetate, carbonate, acetate tetrahydrate, bromide, etc. can be used, or more preferably, sources of cobalt, manganese, and bromine are cobalt acetate tetrahydrate, manganese acetate tetrahydrate, and hydrogen bromide, respectively.

Compounds of Ce, Zr, Hf, Mo, Cr, Fe, W, etc. are preferred for transition metals or lanthanide metals, which are added if necessary. The weight ratio of the added transition metal or lanthanide metal/manganese is preferably 0.001~1. Further, the present invention can be applied to an oxidation reaction by a cobalt-manganese catalyst without bromine as well as to the oxidation reaction by a nickel-manganese-bromine catalyst.

The solvent used in the present invention can be any aliphatic acids of $C_1$~$C_6$, such as formic acid, acetic acid, propionic acid, n-butyric acid, isobutyric acid, pentanoic acid, hexanoic acid, trimethylacetic acid, etc, or more preferably acetic acid or the mixture of acetic acid and water. Preferably, the solvent comprises from 2% to 25%, by weight, of water. The amount of solvent should be 1~10 times the weight of an alkylaromatic compound or the oxidized intermediate compound thereof. Further, the present invention can be applied to the oxidation reaction with water as a solvent.

As for the reaction gas used in the present invention, oxygen, or a gas mixture of oxygen and an inert gas such as nitrogen can be used, or more preferably, a gas mixture of oxygen and carbon dioxide can be used. Preferably, the reaction gas or feed gas lacks an inert diluent. The minimal pressure of the reaction is such that some portions of an alkylaromatic compound or the oxidized intermediate thereof and the solvent are maintained as liquid. The reaction pressure is appropriately 0~35 atm in terms of the gauge pressure or more preferably 8~30 atm.

The amount of carbon dioxide should be 1~80% by volume of the gas, or more preferably 5–50% by volume. As for the method of adding carbon dioxide, it can be supplied in the gas phase at the upper part of the reactor or in the reactants of liquid phase, either periodically or continuously. (For example, carbon dioxide may be added with a gas sparging device into one or more zones of a reactor in a gas phase or liquid phase either periodically, intermittently, or in a continuous manner.) As for the method of supplying carbon dioxide to the reactor, carbon dioxide can be mixed into the reaction gas. Alternatively, the method of recycling the reacted vent gas to the reaction gas can be used for the purpose of utilization of the carbon dioxide and oxygen remaining in the vent gas. (For example, carbon dioxide remaining in the reaction vent gas may be recovered by condensation and recycled to provide carbon dioxide required for the oxidation reaction). When it is supplied to the reactants in liquid, a dip tube, etc. can be used for supplying via bubbling or sparging.

The production method of aromatic carboxylic acids of the present invention could be carried out by a batch type process or a continuous process. The appropriate reaction temperature should be 100~255° C., or more preferably 175~235° C., or most preferably 180~210° C. If the reaction temperature is too low, it is impractical since the reaction rate is too slow. On the other hand, if the reaction temperature is too high, it is non-economical due to the excessive side reactions.

As a reactor, general CSTR (continuous stirred tank reactor) or LOR (liquid oxygen reactor) specially designed to mix liquid oxygen and liquid hydrocarbon substrates without appreciable loss of unreacted oxygen into the overhead vapor space can be used.

According to the present invention, the reaction time is decreased at the same reaction temperature for obtaining the same conversion. At the same reaction time, the present invention requires a lower reaction temperature for a given conversion. The productivity and quality such as chemical impurities can be improved due to the decreased side reactions with the present invention.

The present invention is explained in detail by examples below. Nevertheless, the examples are illustrative only and should not be deemed to limit the present invention.

EXAMPLES 1 THROUGH 10

Production of Isophthalic Acid by the Oxidation of Meta-Xylene for the Fixed Period of Time; the Results are Shown in Table 1.

Example 1

To a titanium pressure reactor, 200 g of reactants were added (i.e., water, meta-xylene, acetic acid, and the catalyst). While stirring, the reaction temperature was raised to 195° C. in the atmosphere of nitrogen. The composition of the reactants was adjusted to 7.5% by weight of water, 15% by weight of meta-xylene, and 77.5% by weight of acetic acid. Based on the total weight of reactants (also referred to as the reaction mixture), the catalyst was comprised of 100 ppm of cobalt, 200 ppm of manganese, and 300 ppm of bromine. Cobalt acetate tetrahydrate, manganese acetate tetrahydrate and hydrogen bromide were used for the catalyst. At the reaction temperature of 195° C., nitrogen was added up to 12.9 atm, and then carbon dioxide was added up to 16.8 atm, and then oxygen was instantaneously added to 28.0 atm so that the concentrations of nitrogen, carbon dioxide, and oxygen in the gas phase became 46, 14, and 40% by volume, respectively. When the reaction pressure reached 28 atm, the amount of consumed oxygen was measured with time, and the oxygen was continuously fed to maintain the same pressure (28 atm) to compensate for the amount of oxygen consumed in the oxidation reaction. After 60 min of reaction, the reactor was allowed to cool to terminate the reaction. The product obtained in this manner was subjected to a solid-liquid separation such as filtration. The solid was dried and analyzed, and the purity of the product was calculated. The experimental conditions, the amount of oxygen consumed, and the purity of isophthalic acid product are compared with those of Comparative Example 1 (which does not employ additional carbon dioxide) in Table 1. The amount of consumed oxygen and the purity of obtained solid product were high compared with those of Comparative Example 1. The results clearly showed that the reaction rate and purity were increased in the presence of carbon dioxide as shown in the run of Example 1, Table 1 as compared with the run without carbon dioxide, e.g. Comparative Example 1.

Example 2

The oxidation reaction of meta-xylene was carried out in the identical manner to Example 1 except that the concentration of the added carbon dioxide was varied to be 7% by volume. In other words, the gas phase was composed of 53% by volume of nitrogen, 7% by volume of carbon dioxide and 40% by volume of oxygen. The results summarized in Table 1 show that the reaction rate and purity are somewhat lower than those in Example 1, but are much higher than those of Comparative Example 1 which does not employ carbon dioxide.

Examples 3 and 4

The oxidation reactions of meta-xylene were carried out in the identical manner to Example 1, except that the concentrations of carbon dioxide in the gas phase was decreased from 14% by volume to 1.8% by volume and 3.5% by volume, and nitrogen was increased from 46% by volume to 58.2% by volume and 56.5% by volume, in Example 3 and 4, respectively. The results are summarized in Table 1, and they show the reaction rates were increased a bit as compared with that of Comparative Example 1. In other words, the rate of the oxidation reaction became faster when meta-xylene was oxidized in the presence of carbon dioxide as compared with Comparative Example 1, which does not employ carbon dioxide. But the acceleration was very small and negligible when the concentration of carbon dioxide was below 4% by volume.

Examples 5 and 6

The oxidation reactions of meta-xylene were carried out in the identical manner to Example 1, except that the concentrations of carbon dioxide in the feed gas were varied from 14% by volume to 5.4% by volume and 50% by volume, and nitrogen was changed from 46% by volume to 54.6% by volume and 10% by volume, in Example 5 and 6, respectively. The results are summarized in Table 1, and they showed the reaction rates were increased as compared with those of Comparative Example 1, and Examples 3 and 4. In other words, the rate of the oxidation reaction became faster when meta-xylene was oxidized in the presence of carbon dioxide as compared with that of Comparative Example 1, which does not employ carbon dioxide. When the concentration of added carbon dioxide was 50% by volume, the purity of the product, i.e. 94.1%, was very high compared with that of Comparative Example 1 (83.6%) and Examples 1 to 5 (86.8–90.2%). The results summarized in Table 1 clearly show that the reaction rate and the purity increase with the concentration of carbon dioxide.

Comparative Example 1

The oxidation reaction of meta-xylene was carried out in the identical manner to Example 1 except that carbon dioxide was not added in the gas phase. In other words, the gas phase comprised 60% by volume of nitrogen and 40% by volume of oxygen. The results are compared in Table 1, and the reaction rate was slower in the comparative run, 589.3 mmol of $O_2$ vs. 592.1–731.6 mmol of $O_2$.

Example 7

The oxidation reaction of meta-xylene was carried out in the identical manner to Example 1 except that the reaction time was changed from 60 min to 90 min. The results summarized in Table 1 clearly show that the reaction rate and purity of the product were high compared with those of Comparative Example 2 without employing carbon dioxide. In other word, the consumed $O_2$ was increased from 673.1 to 788.5 mmol, and the purity increased from 90.3 to 97.6% with the addition of 14% by volume of carbon dioxide in the gas phase.

Comparative Example 2

The oxidation reaction of meta-xylene was carried out in the identical manner to Example 7 except that the carbon dioxide was not added in the gas phase. In other words, the gas phase comprised 60% by volume of nitrogen and 40% by volume of oxygen. The results are compared in Table 1, and the reaction rate was slower in the Comparative run, 673.1 mmol of $O_2$ vs. 788.5 mmol of $O_2$. The purity of the solid product was low in the Comparative run, 90.3% vs. 97.6%.

Examples 8 and 9

The oxidation reaction of meta-xylene was carried out in the identical manner to Example 1 except that the reaction temperature was changed from 195° C. to 185° C. and the reaction time was changed from 60 min to 90 min. The concentrations of added carbon dioxide were 14.0% by volume and 50.0% by volume, and those of nitrogen were 46.0% by volume and 10.0% by volume for Examples 8 and 9, respectively. The results summarized in Table 1 clearly show that the reaction rate and purity of the product were high compared with those of Comparative Example 3, which does not employ carbon dioxide. In other word, the consumed $O_2$ was increased from 652.9 to 720.7–723.2 mmol, and the purity increased from 88.8 to 93.5–93.6% with the addition of 14%–50% by volume of carbon dioxide.

Comparative Example 3

The oxidation reaction of meta-xylene was carried out in the identical manner to Example 8 except that the carbon dioxide was not added in the gas phase. In other words, the gas phase comprised 60% by volume of nitrogen and 40% by volume of oxygen. The results are compared in Table 1 and the reaction rate was slower in the Comparative run, 652.9 mmol of $O_2$ vs. 723.2 mmol of $O_2$. The purity of the solid product was low in the Comparative run, 88.8% vs. 93.5%.

Examples 10

The oxidation reaction of meta-xylene was carried out in the identical manner to Example 1 except that the concentration of catalyst decreased to 85% of Example 1, and 30 ppm of zirconium was added (Co=85, Mn=170, Br=255, Zr=30 ppm). The results summarized in Table 1 clearly show that the reaction rate and purity of the product were higher compared with those of Comparative Example 4, which does not employ carbon dioxide. In other word, the consumed $O_2$ was increased from 599.4 to 660.4 mmol and the purity increased from 84.4 to 89.6% with the addition of 14% by volume of carbon dioxide.

Comparative Example 4

The oxidation reaction of meta-xylene was carried out in the identical manner to Example 10 except that carbon dioxide was not added in the gas phase. In other words, the gas phase comprised 60% by volume of nitrogen and 40% by volume of oxygen. The results are compared in Table 1, and the reaction rate was slower in the Comparative run, 599.4 mmol of $O_2$ vs. 660.4 mmol of $O_2$. The purity of the solid product was low in the Comparative run, 84.4% vs. 89.6%.

TABLE 1

Results of meta-xylene oxidation for the same reaction time.

| | Catalyst System | Reaction Temp.(° C.) /Time(min) | Concentration of carbon dioxide(vol. %) | Amount of Consumed Oxygen(mmol)* | Concentration of Isophthalic Acid in Solid Product (wt. %) |
|---|---|---|---|---|---|
| Example 1 | Co/Mn/Br | 195/60 | 14.0 | 672.7 | 90.2 |
| Example 2 | Co/Mn/Br | 195/60 | 7.0 | 630.5 | 86.8 |
| Example 3 | Co/Mn/Br | 195/60 | 1.8 | 592.1 | |
| Example 4 | Co/Mn/Br | 195/60 | 3.5 | 594.4 | |
| Example 5 | Co/Mn/Br | 195/60 | 5.4 | 616.5 | |
| Example 6 | Co/Mn/Br | 195/60 | 50.0 | 731.6 | 94.1 |
| Comparative Example 1 | Co/Mn/Br | 195/60 | 0 | 589.3 | 83.6 |
| Example 7 | Co/Mn/Br | 195/90 | 14 | 788.5 | 97.6 |
| Comparative Example 2 | Co/Mn/Br | 195/60 | 0 | 673.1 | 90.3 |
| Example 8 | Co/Mn/Br | 185/90 | 14 | 723.2 | 93.5 |
| Example 9 | Co/Mn/Br | 185/90 | 50 | 720.7 | 93.6 |
| Comparative Example 3 | Co/Mn/Br | 185/90 | 0 | 652.9 | 88.8 |
| Example 10 | Co/Mn/Br/Zr | 195/60 | 14 | 660.4 | 89.6 |
| Comparative Example 4 | Co/Mn/Br/Zr | 195/60 | 0 | 599.4 | 84.4 |

* Total oxygen consumption by stoichiometry of the oxidation reaction = 848 mmol

Examples 11 and 12

Oxidation of meta-xylene at the same oxygen consumption level—the oxidation reaction was terminated when the 70% of the theoretical amount of oxygen calculated based on the stoichiometry of the desired oxidation reaction was consumed; the results are shown in Table 2.

Example 11 and 12

The oxidation reaction of meta-xylene was carried out in the identical manner to Example 1, except that the concentration of catalyst decreased to 85% of Example 1, and the concentrations of carbon dioxide were 14%, and 7% by volume, and those of nitrogen were 46% by volume and 53% by volume in Examples 11 and 12, respectively. When the oxygen consumption reached 70% of the theoretical oxygen amount based on the stoichiometry of the desired oxidation reaction, the reactor was allowed to cool to terminate the reaction. It took 58.2 and 62.0 minutes to terminate the reaction, and the concentrations of CO in the gas phase after reaction were 10.7% by volume and 11.5% by volume in Examples 11 and 12, respectively. The results of Table 2 clearly show that the reactivity and selectivity were increased with the addition of carbon dioxide. The increase of reactivity was higher when the reaction time was 60 minutes as compared with 20 or 40 min of reaction.

Comparative Example 5

The oxidation reaction of meta-xylene was carried out in the identical manner to Example 11 except that carbon dioxide was not added in the gas phase. In other words, the gas phase comprised 60% by volume of nitrogen and 40% by volume of oxygen. The results are compared in Table 2 and the reaction rate was slower in the Comparative run, 113.8 min vs. 58.2–62.0 min to reach 70% of oxygen consumption. The concentration of CO was higher in Comparative Example, 12.4% by volume vs. 10.7–11.5% by volume, which showed that the reaction selectivity became lower when carbon dioxide was not added to the gas phase.

TABLE 2

Results of oxidation of meta-xylene at the same oxygen consumption (Reaction was terminated at 70% of the total oxygen consumption based on the stoichiometry of the desired oxidation reaction)

| | Concentration of Carbon Dioxide (vol. %) | Reaction Time (min)* | Consumed Oxygen with Reaction Time (mmol)** | | | Concentration of CO in Gas Phase after Reaction (vol. %) |
|---|---|---|---|---|---|---|
| | | | 20 min | 40 min | 60 min | |
| Example 11 | 14 | 58.2 | 310.3 | 487.3 | >594.0 | 10.7 |
| Example 12 | 7 | 62.0 | 315.5 | 488.1 | 584.5 | 11.5 |
| Comp. Exmp. 5 | 0 | 113.8 | 300.3 | 467.4 | 541.2 | 12.4 |

* Reaction time for 70% of the theoretical oxygen consumption by stoichiometry of the oxidation reaction,
** Theoretical oxygen consumption based on the stoichiometry of the oxidation reaction = 848 mmol.

Examples 13 and 14

Production of Phthalic Acid and Terephthalic Acid by the Oxidation of Ortho-Xylene and Para-Xylene for the Fixed Period of Time; the Results Are Shown in Table 3.

Example 13

The oxidation reaction was carried out in the identical manner to Example 1, except that ortho-xylene was used as a feed instead of meta-xylene, and the reaction temperature was changed from 195° C. to 190° C. 397.2, 519.0, and 569.4 mmol of oxygen were consumed after 20, 40, and 60 min of the reactions, respectively. The results of Table 3, as compared with the Comparative Example 6, clearly show that the reactivity was increased with the addition of carbon dioxide.

Comparative Example 6

The oxidation reaction of ortho-xylene was carried out in the identical manner to Example 13 except that carbon dioxide was not added in the gas phase. In other words, the gas phase comprised of 60% by volume of nitrogen and 40% by volume of oxygen. The results are compared in Table 3 and the reaction rate was slower in the Comparative run from 20 to 60 min of the reaction.

Example 14

The oxidation reaction was carried out in the identical manner to Example 1, except that para-xylene was used as a feed instead of meta-xylene, the reaction temperature was changed from 195° C. to 185° C., and the catalyst concentration was 150 ppm of Co, 300 ppm of Mn, 240 ppm of Br and 24 ppm of Zr. 538.3, 754.2, and 862.1 mmol of oxygen were consumed after 20, 40, and 60 min of the reaction, respectively. The results of Table 3 clearly showed that the reactivity was increased with the addition of carbon dioxide.

Comparative Example 7

The oxidation reaction of para-xylene was carried out in the identical manner to Example 14 except that carbon dioxide was not added in gas phase. In other words, the gas phase comprised 60% by volume of nitrogen and 40% by volume of oxygen. The results are compared in Table 3 and the reaction rate was slower in the Comparative run from 20 to 60 min of the reaction.

dized intermediates are oxidized with a catalyst system, Co—Mn—Br, in the acetic acid medium, with an oxygen feed gas containing a substantial amount of carbon dioxide. (Of course, the aromatic carboxylic acids made by the present invention may be used to make polyester or other products.) This process can also be used to purify crude aromatic carboxylic acid products containing as impurities partially oxidized intermediates of alkyl aromatic compounds to obtain substantially pure aromatic carboxylic acids.

The oxidation reaction of alkylaromatic substrates proceeds more selectively with a much faster rate to produce aromatic carboxylic acid products of improved quality, than the conventional oxidation process. The oxidation reaction occurs under conditions milder than that of the conventional process, and produces aromatic carboxylic acid products of higher purity (containing less impurities such as partially oxidized intermediate oxygenates) in higher yield. In other words, the yield and quality of the aromatic carboxylic acid product such as isophthalic acid and terephthalic acid were improved significantly beyond the current general expectations of the world-wide IPA and PTA (purified terephthalic acid) producers by means of conducting the oxidation reaction with a mixed feed gas containing oxygen and a substantial amount of carbon dioxide in an acetic acid medium under relatively mild conditions. Another catalyst system, in which the cobalt-manganese-bromine system containing an additional transition metal or lanthanide series metal, is also revealed in the present invention.

In conclusion, the present invention discloses for the first time that carbon dioxide functioned as a co-oxidant along with oxygen in the oxidation process of alkylaromatics such as para-xylene. In particular, it was found that in the present invention (a) $CO_2$ is capable of modulating the oxidative property of $O_2$ over the Co—Mn—Br catalyst, (b) the oxidation rate was increased (i.e., enhanced catalytic activity), (c) the oxidation became more selective toward the desired product (i.e., increased selectivity), (d) the reaction product distribution was dramatically altered (i.e., purer production formation), (e) much lower amounts of the partially oxidized products were found in the final acid

TABLE 3

Results of ortho-xylene and para-xylene oxidation for the same reaction time

| | Feed | Catalyst | Reaction Temperature (° C.)/ Reaction time (min) | Concentration of Carbon Dioxide (vol. %) | Consumed Oxygen with Reaction Time (mmol)* | | |
|---|---|---|---|---|---|---|---|
| | | | | | 20 min | 40 min | 60 min |
| Example 13 | Ortho-xylene | Co/Mn/Br | 190/60 | 14 | 397.2 | 519.0 | 569.4 |
| Comparative Example 6 | Ortho-xylene | Co/Mn/Br | 190/60 | 0 | 368.6 | 488.1 | 533.1 |
| Example 14 | Para-xylene | Co/Mn/Br/Zr | 185/60 | 14 | 538.3 | 754.2 | 862.1 |
| Comparative Example 7 | Para-xylene | Co/Mn/Br/Zr | 185/60 | 0 | 425.0 | 653.5 | 815.9 |

*Total oxygen consumption by stoichiometry of the oxidation reaction = 848 mmol

In summary, the present invention discloses an improved process for the production of aromatic carboxylic acids, wherein alkyl aromatic compounds or their partially oxiproduct (thus, the present invention can be used for a purification process of crude terephthalic acid and isophthalic acid), (f) under identical reaction conditions (as compared to the conventional MC-type process), the reaction temperature required to obtain the same level of the conversion (activity) becomes much lower (in other words, the same product yield can be obtained at much lower temperatures, or the product yield can be much higher at the same temperature, and thus a much smaller reactor is required, resulting in an economically more attractive process), (g) a higher concentration of $O_2$ can be used in the reactor without causing an explosion or burning (i.e., safer operation is feasible), and (h) less burning occurs, promoting higher selectivity toward the desired main product, TPA. These findings are believed to be attributed to the generation of a very active oxygen species for the oxidation reaction (the oxygen species being more active than that provided by molecular dioxygen ($O_2$)) created from an intermediate complex of peroxocarbonate form in the co-presence of $CO_2$ and $O_2$ over an MC-type catalyst (cobalt-manganese-bromine), the peroxocarbonate being believed to be of the following form:

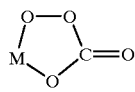

where M is Mn or Co.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method of producing an aromatic carboxylic acid, said method comprising the steps of:

oxidizing an alkyl aromatic compound or a partially oxidized intermediate thereof, with a gas comprising oxygen and at least 4% by volume of the gas of carbon dioxide, using a catalyst comprising cobalt, manganese, and bromine.

2. A method according to claim 1, wherein the catalyst is dissolved in a solvent comprising an aliphatic carboxylic acid having 1 to 6 carbon atoms.

3. A method according to claim 2, wherein the solvent further comprises 2% to 25% by weight of water.

4. A method according to claim 1, wherein the catalyst further comprises another transition metal or a lanthanide metal.

5. A method according to claim 4, wherein the another transition metal or the lanthanide metal is selected from the group consisting of zirconium, hafnium, cerium, molybdenum, chromium, iron, and tungsten.

6. A method according to claim 1, wherein the gas comprises 4% to 80% by volume of the gas of carbon dioxide.

7. A method according to claim 6, wherein the gas comprises 5% to 50% by volume of the gas of carbon dioxide.

8. A method according to claim 7, wherein the gas lacks an inert diluent.

9. A method according to claim 1, wherein the alkyl aromatic compound is selected from the group consisting of para-xylene, meta-xylene, ortho-xylene, pseudocumene (1,2,4-trimethylbenzene), mesitylene (1,3,5-trimethylbenzene), durene (1,2,4,5-tetramethylbenzene), pentamethylbenzene, hexamethylbenzene, dimethylnaphthalene, 4,4'-dimethylbiphenyl, and toluene.

10. A method according to claim 1, wherein the partially oxidized alkyl aromatic intermediate is selected from the group consisting of para-toluic acid, meta-toluic acid, ortho-toluic acid, para-tolualdehyde, meta-tolualdehyde, ortho-tolualdehyde, 4-carboxybenzaldehyde, 3-carboxylbenzaldehyde, and 2-carboxybenzaldehyde.

11. A method according to claim 10, wherein the partially oxidized alkyl aromatic intermediate is selected from the group consisting of para-toluic acid, meta-toluic acid, 4-carboxybenzaldehyde, and 3-carboxybenzaldehyde.

12. A method according to claim 1, wherein the aromatic carboxylic acid is selected from the group consisting of terephthalic acid, isophthalic acid, phthalic acid, phthalic anhydride, naphthalene dicarboxylic acid, trimellitic acid, trimellitic anhydride, trimesic acid, pyromellitic dianhydride, benzene pentacarboxylic acid, benzene hexacarboxylic acid, 4,4'-biphenyldicarboxylic acid, and benzoic acid.

13. A method according to claim 12, wherein the aromatic carboxylic acid is selected from the group consisting of terephthalic acid, isophthalic acid, and phthalic anhydride.

14. A method according to claim 1, wherein the carbon dioxide is added with a gas sparging device into one or more zones of a reactor in a gas phase or liquid phase either periodically, intermittently, or in a continuous manner.

15. A method according to claim 1, wherein the carbon dioxide is mixed into the gas, which is a feed gas.

16. A method according to claim 1, wherein carbon dioxide remaining in reaction vent gas is recovered by condensation and is recycled to provide the carbon dioxide required for the oxidation reaction.

17. A method according to claim 1, wherein the alkyl aromatic compound para-xylene is used to produce the aromatic carboxylic acid terephthalic acid, and the catalyst is prepared by combining cobalt acetate tetrahydrate, manganese acetate tetrahydrate, and hydrogen bromide.

18. A method according to claim 1, wherein the alkyl aromatic compound meta-xylene is used to produce the aromatic carboxylic acid isophthalic acid, and the catalyst is prepared by combining cobalt acetate tetrahydrate, manganese acetate tetrahydrate, and hydrogen bromide.

19. A method according to claim 1, wherein the alkyl aromatic compound ortho-xylene is used to produce the aromatic carboxylic acid phthalic acid or phthalic anhydride, and the catalyst is prepared by combining cobalt acetate tetrahydrate, manganese acetate tetrahydrate, and hydrogen bromide.

20. A method of producing an aromatic carboxylic acid, said method comprising the steps of:

oxidizing an alkyl aromatic compound or a partially oxidized intermediate thereof, with a gas comprising oxygen and an effective amount of carbon dioxide, the effective amount being an amount sufficient to exhibit action by the carbon dioxide as a co-oxidant, using a catalyst comprising at least one transition metal.

21. A process of purifying crude terephthalic acid or crude isophthalic acid products containing, as an impurity, a partially oxidized intermediate of an alkyl aromatic compound, to obtain substantially pure terephthalic acid or isophthalic acid using the method according to claim 10.

22. A process according to claim 21, wherein the partially oxidized intermediate of an alkyl aromatic compound is selected from the group consisting of 4-carboxybenzaldehyde and 3-carboxybenzaldehyde.

* * * * *

UNITED STATES PATENT AND TRADEMARK OFFICE
CERTIFICATE OF CORRECTION

PATENT NO. : 6,180,822 B1
DATED : January 30, 2001
INVENTOR(S) : Sung-Hwa Jhung et al.

Page 1 of 1

It is certified that error appears in the above-identified patent and that said Letters Patent is hereby corrected as shown below:

Column 2,
Line 54, "have" should read -- has --.

Column 6,
Line 62, "was" should read -- were --.

Column 8,
Line 9, "word" should read -- words --.
Line 35, "Examples 10" should read -- Example 10 --.

Column 11,
Line 20, "comprised of" should read -- comprised --.

Signed and Sealed this

Thirtieth Day of April, 2002

*Attest:*

*Attesting Officer*

JAMES E. ROGAN
*Director of the United States Patent and Trademark Office*